United States Patent [19]

Secoy

[11] Patent Number: 5,000,045
[45] Date of Patent: Mar. 19, 1991

[54] ACOUSTIC EMISSION WAVEGUIDE

[75] Inventor: Todd C. Secoy, Cupertino, Calif.

[73] Assignee: Ford Aerospace Corporation, Palo Alto, Calif.

[21] Appl. No.: 455,461

[22] Filed: Dec. 21, 1989

[51] Int. Cl.[5] .............................................. G01P 29/24
[52] U.S. Cl. ....................................... 73/587; 73/644; 73/801
[58] Field of Search .................... 73/571, 587, 644, 801

[56] References Cited

U.S. PATENT DOCUMENTS

| | | | |
|---|---|---|---|
| 4,392,380 | 7/1983 | Caines | 73/644 |
| 4,510,812 | 4/1985 | Feng | 73/644 |
| 4,671,114 | 6/1987 | Litzkow et al. | 73/587 |
| 4,783,997 | 11/1988 | Lynnworth | 73/644 |

Primary Examiner—Hezron E. Williams
Assistant Examiner—Rose M. Finley
Attorney, Agent, or Firm—Rosenblum, Parish & Bacigalupi

[57] ABSTRACT

An acoustic emission waveguide (10) for holding a test sample (29) in a hostile environment and guiding ultrasonic waves to a transducer (34) disposed in a non-hostile environment. The waveguide (10) includes a flattened test sample attachment end (15) having a flat bar clamp (22) to hold test specimens (29) thereto. The transducer attachment end (17) includes a clamp (32) which holds the transducer (34) firmly against the waveguide end (17) and against a threaded nut (30) which increases the surface area of the end (17) of the waveguide, such that enhanced acoustic transmission to the transducer (34) is achieved. A couplant grease is utilized in the test sample clamp (20) and in the transducer attachment clamp (32) to enhance the transmission of acoustic energy from the test sample (29) to the waveguide rod (12) and from the rod (12) to the transducer (34).

25 Claims, 2 Drawing Sheets

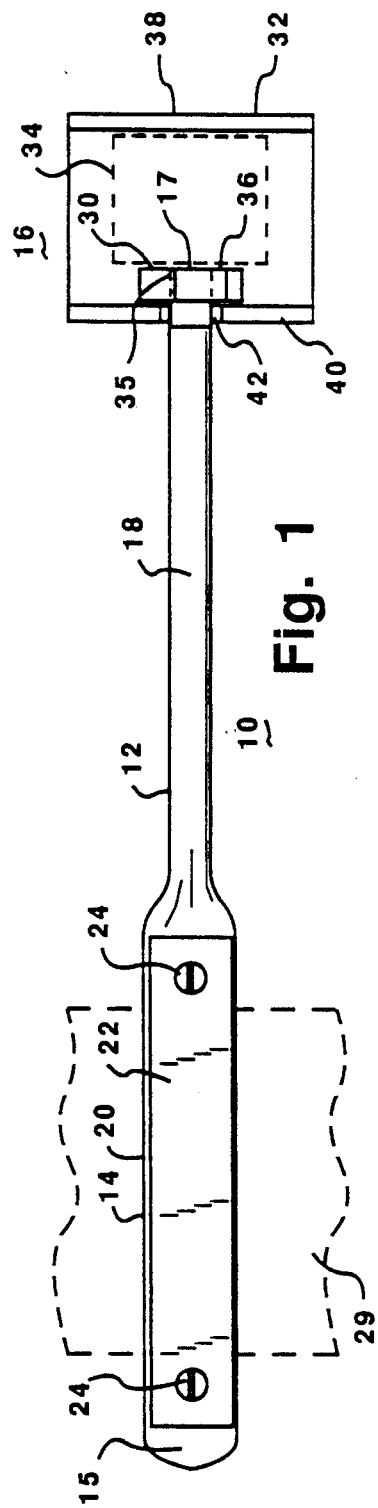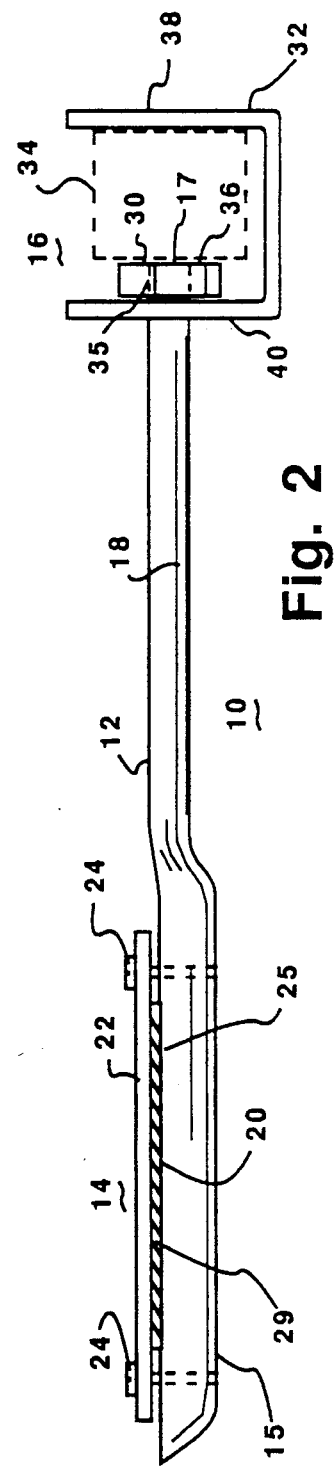

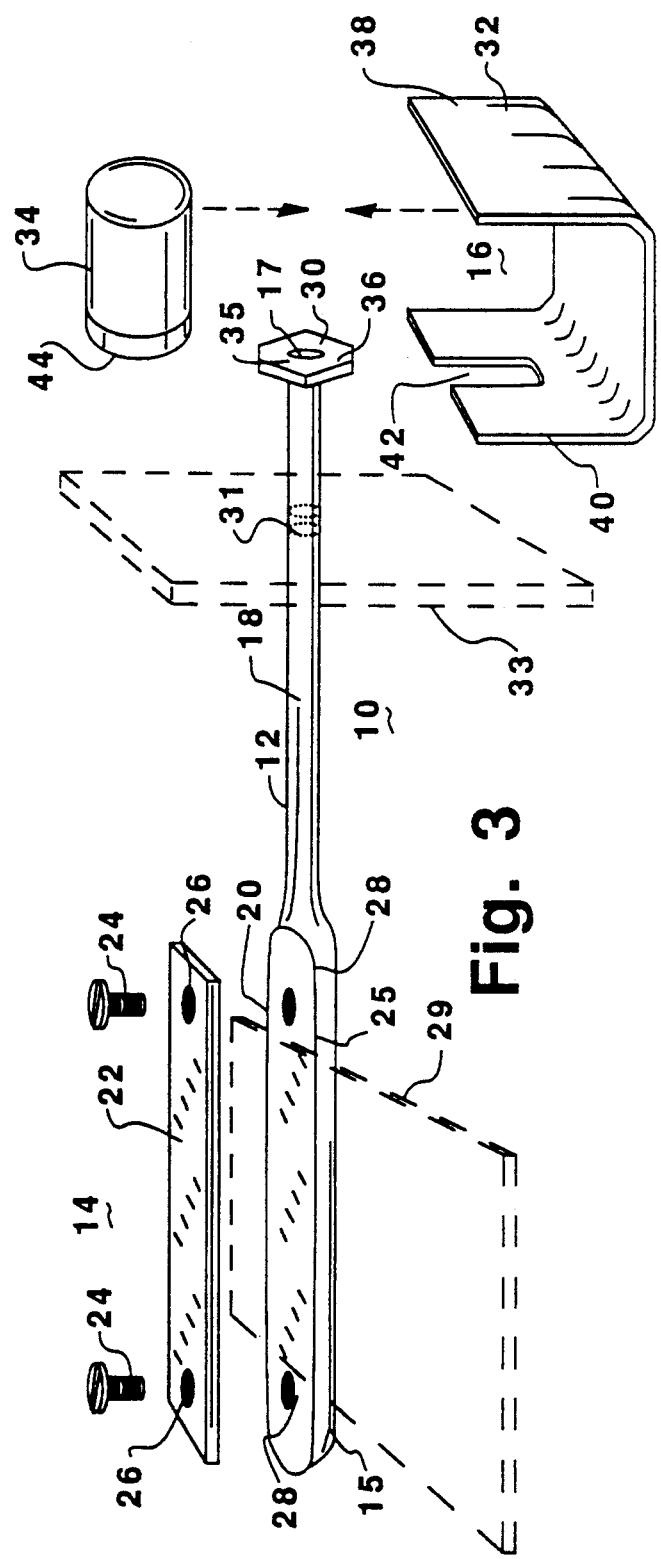

ACOUSTIC EMISSION WAVEGUIDE

BACKGROUND OF THE INVENTION

1. Field of the Invention

The present invention relates generally to ultrasonic waveguides and more particularly to an acoustic emission waveguide adapted for physically holding a specimen in a thermally hostile environment and transmitting the acoustic emission response of the specimen through the waveguide to a transducer located in a non-hostile environment.

2. Description of the Prior Art

The present invention is utilizable where a test specimen is to be located in a hostile environment, such as a thermal environment chamber, and it is desired to locate a transducer outside the chamber in a non-hostile environment at room temperature and means are required for guiding ultrasonic energy from the sample to the sensing transducer. The most relevant known prior art is disclosed in U.S. Pat. No. 4,510,812, issued Apr. 16, 1985 to Feng and in U.S. Pat. No. 4,392,380, issued July 12, 1983 to Caines. Both references teach acoustic waveguides utilized where a specimen is to be located in a hostile environment and the transducer is located in a non-hostile environment. These prior art devices both use rather complicated methods of attachment of the specimen to the waveguide.

Feng employs a dry coupling technique utilizing a magnetic mounting fixture, or an adhesively bonded mounting fixture, which holds the tip of the waveguide against the specimen utilizing pressure from a coiled spring. The disclosed device requires either a ferromagnetic surface or one which will not be affected by adhesive bonding. The device is not well suited for low temperature exposures because adhesives are very active sources of acoustic emissions and can mask the emissions from the specimen.

Caines utilizes a U-shaped clamp which surrounds the test specimen and employs a type of dry coupling in which a malleable copper foil is used to make good conformal contact between the test specimen and the tip of the waveguide. This technique requires very high pressure to promote good coupling. Such devices are thus not suited for testing many types of specimens.

SUMMARY OF THE INVENTION

The acoustic emission waveguide (10) of the present invention includes an acoustic transmission rod (12) having a test sample attachment fixture (20) (22) disposed at one end (15) thereof and a transducer attachment fixture (32) disposed at the other end (17). The length of the transmission rod (12) is dependent upon the particular test apparatus used and must be long enough so that the sample (29) may be held by the sample fixture in a hostile environment (such as a cryogenic chamber) while the transducer (34) is held in a non-hostile environment, such as ambient laboratory conditions. In the preferred embodiment, a side surface (20) of one end (15) of the waveguide is machined flat along a segment of its length to facilitate the attachment of flat test specimens (29) thereto. The other end (17) of the waveguide has a nut (30) threaded onto the end (17) of the rod, and the end surface 36 of the nut 30 and the end surface of the rod end 17 are both machined flat to mate with the surface of an acoustic emission transducer (34). A flat clamp member (22) is utilized to hold the test specimen (29) to the waveguide rod (12). The coupling of the test specimen with the waveguide is enhanced by utilizing a couplant grease (25) therebetween. The transducer (34) is held against the end (17) of the waveguide rod (12) utilizing a clamping bracket (32) which holds the transducer tightly against the end (17) of the waveguide, such that good transmission of the acoustic waves is facilitated.

An important advantage of the present invention is that it provides an acoustic emission waveguide to which a specimen is easily attached.

Another advantage of the present invention is that it provides an acoustic emission waveguide which provides for easy installation of a transducer.

It is a further advantage of the present invention that it provides an acoustic emission waveguide with a large surface area for mating with the specimen so that good transmission from the specimen to the waveguide is achieved.

The foregoing and other features and advantages of the present invention will be apparent from the following detailed description of the preferred embodiment which makes reference to the several figures of the drawing.

IN THE DRAWING

FIG. 1 is a top plan view of the acoustic emission waveguide of the present invention;

FIG. 2 is a side elevational view of the present invention; and

FIG. 3 is an exploded perspective view of the present invention individually showing each component thereof.

DESCRIPTION OF THE PREFERRED EMBODIMENT

As depicted in FIGS. 1, 2 and 3 of the drawing, the acoustic emission waveguide 10 of the present invention includes a rod-like member 12 having a test sample attachment means 14 disposed at one end 15, an acoustic detector attachment means 16 disposed at the other end 17, and a cylindrical body portion 18 disposed between the ends 15 and 17. The waveguide rod member 12 is made from a long, narrow, solid, cylindrical rod, which in the preferred embodiment is composed of stainless steel. The test sample attachment means 14 includes a portion of the rod 12 that is flattened to an elongated test sample attachment surface 20 disposed along the length of the rod 12. An elongated generally flat, rectangular test sample clamping bar 22 is also provided. In the preferred embodiment the attachment of bar 22 to the waveguide rod 12 is achieved through the utilization of screws 24 which pass through holes 26 formed in the clamping bar 22, and which screws are threadably engagable in threaded holes 28 formed in the flattened surface 20 of the waveguide rod 12.

A test sample 29, shown in phantom, which preferably consists of a flat piece of material, will be positioned upon the surface 20 and under the clamp bar 22. The test sample 29 is engaged to the test sample attachment means 14 of the waveguide rod 12 by the tightening of the screws 24 whereby clamp 22 is drawn toward the flat surface 20.

In the preferred embodiment, a couplant grease 25 is applied to the flat surface 20 prior to the clamping attachment of a test sample thereto. The couplant grease 25 serves to enhance the transmission of ultrasonic energy between the test sample and the flat surface 20 of the waveguide rod 12. Additionally, the relatively large area of contact that the flat surface 20 provides with the test sample further enhances the quality of ultrasonic transmission between the test sample and the waveguide rod 12. The couplant grease 25 must be suited for use throughout the temperature ranges that will be experienced in a particular test. That is, it must not solidify at low temperatures nor flow at high temperatures. In the preferred embodiment a grease that meets the U.S. Military Specification MIL-A-907, such as the lead-based grease, LED-PLATE anti-seize compound No. 250 from Armite Laboratories, Los Angeles, Calif., is utilized.

The body portion 18 of the waveguide rod 12 is preferably circular in cross-section and is formed with a relatively narrow diameter, such that only a small hole 31 need be formed in the wall 33, shown in phantom in FIG. 3, of a test chamber, so that the detector attachment means 16 of the waveguide rod 12 may protrude into the ambient laboratory environment while the test sample attachment means 14 resides in the hostile environment of the chamber.

The detector attachment means 16 of the waveguide 12 includes a threaded nut 30 that is threadably engaged with threads 35 formed in the end 17 of the rod 12. When the nut 30 is removed from its engagement with the end 17, the body portion 18 of the rod 12 may be inserted through the relatively small hole 31 in the wall 33 of the test chamber. With the nut 30 in place on the end 17 of rod 12, a resilient metal clamp 32 is utilized to hold an acoustic detector such as a transducer 34 against the end 17 of the rod 12. In the preferred embodiment, the outer surface 36 of the nut 30 is machined to be flat and co-planar with the end 17 of the rod 12 when the nut 30 is threadably engaged thereon. The end 17 of the rod 12 is threaded only to the width of the nut 30, such that the co-planar relationship of the nut surface 36 with the end 17 of the rod 12 is achieved when the nut 30 is threadably engaged upon the rod 12. It is within the contemplation of the invention that other ways of achieving a co-planar relationship of the nut surface 36 with the rod end 17 may be utilized.

In the preferred embodiment, the clamp 32 is a resilient metal bracket, preferably composed of aluminum, that is formed in a U-shaped configuration. One leg 38 of the U-shaped clamp 32 is disposed behind the transducer 34 while the other leg 40 of the U-shaped clamp 32 is formed with a slot 42 of sufficient width to permit the body portion 18 of the waveguide rod 12 to reside therein, while preventing the nut 30 from passing therethrough.

When the transducer 34 is disposed within the clamp 32, the rearward leg 38 of the clamp 32 will provide a spring force so that the sample end 44 of the transducer 32 may be pressed into direct contact with the end 17 of the waveguide rod 12 by the spring force of the clamp 32.

The attachment of the nut 30 with the end 17 acts as an acoustic signal transmission enhancement means that facilitates the transmission of acoustic waves to the transducer sample end 44, because the flat outer surface 36 of the nut 30 makes direct contact with the sample end 44 of the transducer 34, thus providing an enlarged surface area for contact between the transducer 34 and the waveguide rod 12. In the preferred embodiment a couplant grease is utilized between the sample end 44 of the transducer 34 and the flat surface 36 of the nut 30 The type of couplant grease utilized in this environment need not meet the stringent temperature specifications of the couplant grease utilized in the sample attachment means 14; however, the use of the previously identified couplant grease is suitable in this location also.

While the invention has been shown and described with reference to a particular preferred embodiment, it will be understood by those skilled in the art that various alterations and modifications in form and detail may be made therein. Accordingly, it is intended that the following claims cover all such alterations and modifications as may fall within the true spirit and scope of the invention.

What I claim is:

1. A waveguide for transmitting acoustic emissions from a test sample, comprising:
    a rod-like member having a first end and a second end, and a body portion disposed between said first end and said second end;
    a test sample attachment means being engaged to said first end and formed for the attachment of a test sample thereto;
    an acoustic detector attachment means being engaged to said second end for the attachment of a detector to said second end;
    an acoustic signal transmission enhancement means, said enhancement means being removably engagable with said second end of said rod-like member, and functioning to engage said detector to provide enhanced acoustic signal transmission to said detector; and
    wherein said acoustic signal transmission enhancement means includes a threaded nut and mating threads being formed on said second end of said rod-like member.

2. A waveguide as described in claim 1 wherein said nut includes a flat surface being formed thereon for mating engagement with said detector.

3. A waveguide as described in claim 2 wherein said second end is formed with a flat surface, and said nut is engaged with said second end such that said flat surface of said nut and said flat surface of said second end are disposed in a co-planar relationship when said nut is threadably engaged to said second end of said rod-like member.

4. A waveguide for transmitting acoustic emissions from a test sample, comprising:
    a rod-like member having a first end and a second end, and a body portion disposed between said first end and said second end;
    a test sample attachment means being engaged to said first end and formed for the attachment of a test sample thereto;
    an acoustic detector attachment means being engaged to said second end for the attachment of a detector to said second end;
    an acoustic signal transmission enhancement means, said enhancement means being removably engagable with said second end of said rod-like member, and functioning to engage said detector to provide enhanced acoustic signal transmission to said detector;
    wherein said test sample attachment means includes a flattened portion of said waveguide proximate said first end that is adapted or the attachment of a test specimen thereto; said test specimen attachment means further including a test specimen clamping means being removably engagable with said rod-like member for releasably holding said test specimen against said flattened portion of said waveguide; and said test specimen clamping means including an elongated bar having a flat face of substantially the same size as said flattened portion of said waveguide, said specimen clamping means having an attachment means for drawing said flat face of said bar towards said flattened portion of said waveguide, such that a test specimen disposed therebetween will be firmly held against said flattened portion of said waveguide.

5. A waveguide for transmitting acoustic emissions from a test sample, comprising:
a rod-like member having a first end and a second end, and a body portion disposed between said first end and said second end;
a test sample attachment means being engaged to said first end and formed for the attachment of a test sample thereto;
an acoustic detector attachment means being engaged to said second end for the attachment of a detector to said second end;
an acoustic signal transmission enhancement means, said enhancement means being removably engagable with said second end of said rod-like member, and functioning to engage said detector to provide enhanced acoustic signal transmission to said detector;
wherein said second end is formed with a flattened end surface for the engagement of said detector thereto; and
said acoustic detector attachment means includes a detector clamp being engagable with said rod-like member and with said detector to create a pressed engagement of said detector with said flattened end surface of said second end; said detector clamp including a U-shaped member having two legs, one of said legs being disposed to press said detector into physical contact with said flattened end surface of said second end, and the other of said legs being disposed to make contact with said acoustic signal transmission enhancement means.

6. A waveguide for transmitting acoustic emissions from a test sample, comprising:
a rod-like member having a first end and a second end and a body portion disposed between said first end and said second end;
a test sample attachment means being engaged proximate said first end for the attachment of a test sample to said waveguide; said test sample attachment means including a flattened first surface portion of said waveguide formed proximate said first end that is adapted to the attachment of a test specimen thereto; said test specimen attachment means further including a test specimen clamping means being removably engagable with said rod-like member for releasably holding said test specimen against said first surface;
an acoustic detector attachment means being engaged to said rod-like member proximate said second end for the attachment of an acoustic detector to said second end; said rod-like member including a flattened end surface formed at said second end for the engagement of said detector thereto, and said detector attachment means also including a detector clamp being engagable with said rod-like member and with said detector to create a pressed engagement of said detector with said flattened second end surface of said rod-like member.

7. A waveguide as described in claim 6, further including a removably engagable acoustic signal transmission enhancement means, said enhancement means being removably engagable with said second end portion of said rod-like member, and formed to engage said detector to provide enhanced acoustic signal transmission to said detector.

8. A waveguide as described in claim 7 wherein said signal transmission enhancement means includes a threaded nut and mating threads being formed on said second end of said rod-like member.

9. A waveguide as described in claim 8 wherein said nut includes a flat surface being formed thereon for mating engagement with said detector.

10. A waveguide as described in claim 9 wherein said second end is formed with a flat surface, and said nut is engaged with said second end portion such that said surface of said nut and said flat surface of said second end are disposed in a co-planar relationship when said nut is threadably engaged to said second end of said rod-like member.

11. A waveguide as described in claim 6 wherein said specimen clamping means includes an elongated bar having a flat face of substantially the same size as said first surface, said specimen clamping means having an attachment means for drawing said flat face of said bar toward said first surface of said rod-like member such that a test specimen disposed therebetween will be firmly held against said first surface of said rod-like member.

12. A waveguide as described in claim 11, further including a removably engagable acoustic signal transmission enhancement means, said enhancement means being removably engagable with said second end of said rod-like member, and formed to engage said detector to provide enhanced acoustic signal transmission to said detector.

13. A waveguide as described in claim 12 wherein said signal transmission enhancement means includes a threaded nut and mating threads being formed on said second end of said rod-like member.

14. A waveguide as described in claim 13 wherein said nut includes a flat surface being formed thereon for mating engagement with said detector.

15. A waveguide as described in claim 14 wherein said second end is formed with a flat surface, and said nut is engaged with said second end such that said surface of said nut and said flat surface of said second end are disposed in a co-planar relationship when said nut is threadably engaged to said second end of said rod-like member.

16. A waveguide as described in claim 6 wherein said detector clamp means includes a U-shaped member having two legs, one of said legs being disposed to press said detector into physical contact with said flattened end surface of said second end, and the other of said legs being disposed to engage said second end.

17. A waveguide as described in claim 16, further including a removably engagable acoustic signal transmission enhancement means, said enhancement means being removably engagable with said second end of said rod-like member, and formed to engage said detector to provide enhanced acoustic signal transmission to said detector.

18. A waveguide as described in claim 17 wherein said signal transmission enhancement means includes a threaded nut and mating threads being formed on said second end of said rod-like member.

19. A waveguide as described in claim 18 wherein said nut includes a flat surface being formed thereon for mating engagement with said detector.

20. A waveguide as described in claim 19 wherein said second end of said rod-like member is formed with a flat surface, and said nut is engaged with said second end such that said surface of said nut and said flat surface of said second end are disposed in a co-planar relationship when said nut is threadably engaged to said second end of said rod-like member.

21. A waveguide as described in claim 6 wherein said specimen clamping means includes an elongated bar having a flat face of substantially the same size as said flattened first surface portion of said rod-like member, said specimen clamping means having an attachment means for drawing said flat face of said bar toward said first surface such that a test specimen disposed therebetween will be firmly held against said first surface;

said detector clamp means including a U-shaped member having two legs, one of said legs being disposed to press said detector into physical contact with said second end of said rod-like member, and the other of said legs being disposed to engage said second end of said rod-like member.

22. A waveguide as described in claim 21, further including a removably engagable acoustic signal transmission enhancement means, said enhancement means being removably engagable with said second end of said rod-like member, and formed to engage said detector to provide enhanced acoustic signal transmission to said detector.

23. A wave guide as described in claim 22 wherein said signal transmission enhancement means includes a threaded nut and mating threads being formed on said second end of said rod-like member.

24. A waveguide as described in claim 23 wherein said nut includes a flat surface being formed thereon for mating engagement with said detector.

25. A waveguide as described in claim 24 wherein said second end is formed with a flat surface, and said nut is engaged with said second end such that said surface of said nut and said flat surface of said second end are disposed in a co-planar relationship when said nut is threadably engaged to said second end of said rod-like member.

* * * * *